United States Patent [19]

Babb et al.

[11] Patent Number: 5,215,925
[45] Date of Patent: Jun. 1, 1993

[54] METHOD AND COMPOSITION FOR MAGNESIUM ION DETECTION USING HYDROXY-SUBSTITUTED CYANOFORMAZANS

[75] Inventors: Bruce E. Babb, Rochester; David A. Hilborn, Henrietta, both of N.Y.

[73] Assignee: Eastman Kodak Company, Rochester, N.Y.

[21] Appl. No.: 716,587

[22] Filed: Jun. 17, 1991

Related U.S. Application Data

[63] Continuation of Ser. No. 857,001, Apr. 29, 1986, abandoned.

[51] Int. Cl.$^5$ .................. G01N 31/22; G01N 33/20; C07C 245/00
[52] U.S. Cl. ............................ 436/74; 436/79; 534/652
[58] Field of Search ............... 534/652; 436/74, 79

[56] References Cited

U.S. PATENT DOCUMENTS

| | | |
|---|---|---|
| 3,663,525 | 5/1972 | Witterholt et al. ............ 534/652 |
| 4,383,043 | 5/1983 | Denney et al. ................ 436/74 |
| 4,503,156 | 3/1985 | Yamazato et al. ............. 436/79 |
| 4,753,890 | 6/1988 | Smith-Lewis et al. .......... 436/74 |

FOREIGN PATENT DOCUMENTS

244196 11/1987 European Pat. Off. ............ 534/652

OTHER PUBLICATIONS

Budesinsky et al, *Inorg. Chem.*, 10 (2), pp. 313-317 (1971).
Podchainova et al, *Zhur. Analiticheskoi Khimii*, 32 (4), pp. 822-832 (1977).
Malevannyi et al, *Tr. Inst. Khim. Ural. Nauchn. Tsentr. Akad. Nauk SSSR*, 30 pp. 55-61 (1974)—Abstract Only.
Malevannyi et al, *Izv. Tomsk. Politekh. Inst.*, 238, pp. 86-88 (1977)—Abstract Only.
Krupina et al, *Khim. Prom-st., Ser.: Fosfurnaya Prom-st.*, 5 oo, 13-17 (1979)—Abstract Only.
Wizinger et al, *Helv. Chimica Acta.*, 36, pp. 531-536 (1953).
Fung et al, *Chemical Reagents*, 4 (4), pp. 219-222 (1982).
Yu et al, *Analytical Chemistry*, 11 (3), pp. 187-192 (1982).
Yu et al, *Chem. J. of Chinese Universities*, 4 (2), pp. 185-188 (1983).
Webster's Third New International Dictionary, G. & C. Merriam Co., Mass., 1961; p. 2287.

*Primary Examiner*—Mary C. Lee
*Assistant Examiner*—Fiona T. Powers
*Attorney, Agent, or Firm*—J. Lanny Tucker

[57] ABSTRACT

1,5-Bis(2-hydroxyphenyl)-3-cyanoformazans substituted in at least one of the 3-, 4- and 5-positions of either phenyl moiety are useful for the determination of magnesium ions. The cyanoformazan substituents are chosen such that their cumulative Hammett-sigma value is greater than about 0.23. These cyanoformazans are useful in analytical compositions and methods for either wet or dry assay of magnesium ions.

9 Claims, 1 Drawing Sheet

METHOD AND COMPOSITION FOR MAGNESIUM ION DETECTION USING HYDROXY-SUBSTITUTED CYANOFORMAZANS

This is a continuation of application Ser. No. 857,001, filed Apr. 29, 1986, now abandoned.

FIELD OF THE INVENTION

This invention relates to clinical chemistry. More specifically, it relates to novel cyanoformazan compounds and their use in analytical compositions and methods for the determination of magnesium ions.

BACKGROUND OF THE INVENTION

Magnesium in its ionic form is essential to many physiological processes. It is one of the most abundant cations in the body and, next to potassium, it is the most prevalent intracellular ion. It plays a vital role in carbohydrate and lipid metabolism by serving as an activator of adenosine triphosphate (ATP) in the transfer of energy rich phosphate. It is also essential as an activating ion for many enzymes involved in lipid, carbohydrate and protein metabolism. In muscle tissue, magnesium has a significant influence on neuromuscular apparatus.

The amount of magnesium in the body is particularly significant. Decreased levels of magnesium in the body produce muscle irritability which, if not corrected, can result in involuntary muscle spasms and convulsions. On the other hand, increased levels of magnesium can result in a loss of deep tendon reflexes, a loss of touch, temperature and pain sensation, respiratory failure and cardiac arrest.

Therefore, it has been long recognized that for suitable diagnosis and treatment of various ailments, the accurate and rapid measurement of magnesium ions is important. In addition, it is also important in many environmental monitoring programs and manufacturing processes that magnesium be accurately measured.

Colorimetric methods are known for the determination of the concentration of magnesium ions in various fluids, e.g. groundwater, seawater, wastewater, manufacturing liquids and biological fluids. These methods usually involve adding a reagent to the fluid which forms a colored complex with any magnesium ions present. The complex absorbs electromagnetic radiation at a characteristic wavelength different from that of uncomplexed reagent.

Known methods for determining magnesium have various drawbacks. The fluids to be tested often contain various materials which interfere with the assay. For example, proteins and calcium ions present in fluids can also complex with magnesium complexing dyes, thereby causing an interference.

Hydroxy-substituted cyanoformazan derivatives have been used in the analysis of ions in fluids for some time, as described by Budesinsky et al, *Inorg. Chem.*, 10(2), 313-317 (1971) and Podchainova et al, *Zhur. Analiticheskoi Khimii*, 32(4), 822-832 (1977). These references describe the complexation properties of several cyanoformazans with various metal ions. One compound specifically described by both references is 1,3-bis(2-hydroxy-5-sulfophenyl)-3-cyanoformazan. While this compound was found to successfully complex with chromium, copper, nickel and a variety of other transition metal ions, it does not selectively complex with magnesium ions at relatively low pH (i.e. less than 10). Other similar cyanoformazans known to complex aluminum ions at pH 4 are described by Malevannyi in *Tr. Inst. Khim. Ural. Nauchn. Tsentr, Akad. Nauk SSSR*, 30, pp. 55-61 (1974) and *Izv. Tomsk. Politekh. Inst.*, 238, pp. 86-88 (1977). No complexation of magnesium ions is described or suggested in any of these references.

Other cyanoformazan derivatives are described by Feng et al in the Chinese journal *Chemical Reagents*, 4(4), pp. 219-222 (1982). This reference describes an evaluation of the effect of surfactants on 1,5-bis(2-hydroxy-5-sulfophenyl)-3-cyanoformazan and 1,5-bis(2-hydroxy-5-chlorophenyl)-3-cyanoformazan. However, these compounds must be used at relatively high pH, i.e. greater than 10, for greatest sensitivity for magnesium ions. At a pH below 10, their selectivity for magnesium is low. Further, the 5-sulfophenyl derivative exhibits high background in a magnesium assay. Also, the stability of the dyes decreases with increasing pH, i.e. they tend to break down at higher pH and cannot be stored for an extended period of time.

Hence, there is a need in the art for compounds which have high sensitivity for magnesium ions at relatively low pH.

SUMMARY OF THE INVENTION

The problems noted above are overcome with a method for the determination of magnesium ions comprising the steps of:

A. at a pH of from about 8.5 to about 10.5, contacting a sample of a liquid suspected of containing magnesium ions with a 1,5-bis(2-hydroxyphenyl)-3-cyanoformazan substituted in at least one of the 3-, 4- and 5-positions of either phenyl moiety with a substituent such that the cumulative Hammett-sigma value of the substituents is greater than about 0.23, the cyanoformazan being capable of complexing with magnesium ions at a pH of from about 8.5 to about 10.5, and B. detecting the color change resulting from the complexing of magnesium ions with the cyanoformazan.

This invention also provides a composition for the determination of magnesium ions buffered to a pH of from about 8.5 to about 10.5 and comprising a nonionic or anionic surfactant and a 1,5-bis(2-hydroxyphenyl)-3-cyanoformazan substituted in at least one of the 3-, 4- and 5-positions of either phenyl moiety with a substituent such that the cumulative Hammett-sigma value of the substituents is greater than about 0.23, the cyanoformazan being capable of complexing with magnesium ions at a pH of from about 8.5 to about 10.5.

Further, a novel class of compounds includes 1,5-bis(2-hydroxyphenyl)-3-cyanoformazans substituted in at least one of the 3-, 4- and 5-positions of either phenyl moiety with a substituent such that the cumulative Hammett-sigma value of the substituents is greater than about 0.35, provided that none of the substituents is carboxy or nitro, the cyanoformazan being capable of complexing with magnesium ions at a pH of from about 8.5 to about 10.5.

The present invention provides a number of advantages. Generally, it can be used to determine magnesium ions in various liquids at a pH of from about 8.5 to about 10.5. In this pH range, the cyanoformazan compounds have excellent stability and high selectivity for magnesium ions. It is preferable to carry out magnesium assays at a pH below 10.5 because at the higher pH, the assay is likely to have higher background from dye instability. Also, in the dry assays, it is difficult to control keeping when the element is designed for high pH assay.

With the novel compounds of this invention, which are preferred in the practice of the assay, the color change resulting from the presence of magnesium ions can be readily detected at longer wavelengths, i.e. greater than 600 nm, thereby minimizing the background problem. It has also been observed that many of these compounds exhibit reduced affinity for complexation with protein molecules, thereby reducing the potential for protein interference.

BRIEF DESCRIPTION OF THE DRAWING

The FIGURE is a plot of absorbance scans for a cyanoformazan dye alone and the dye complexed with magnesium ions as described in Example 10 below.

DETAILED DESCRIPTION OF THE INVENTION

Figure 1:
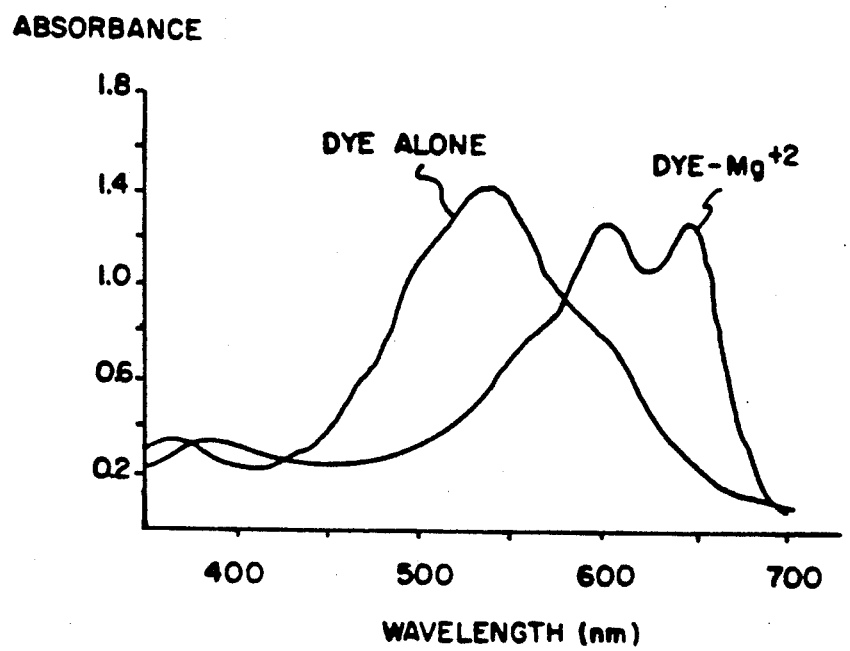

The compounds useful in this invention are 1,5-bis(2-hydroxyphenyl)-3-cyanoformazans which are substituted in at least one of the 3-, 4- and 5-positions of either phenyl moiety with a substituent such that the cumulative Hammett-sigma value of the substituents is greater than about 0.23 which is approximately the Hammett-sigma value for a single chloro substituent in either the 3- or 5-position. In a preferred embodiment using the novel compounds of this invention, the cumulative Hammett-sigma value is greater than about 0.35. It is critical that the cyanoformazans described herein be capable of complexing with magnesium ions at a pH of from about 8.5 to about 10.5. Such complexing property can be readily evaluated by putting a given compound in a solution buffered to a pH of from about 8.5 to about 10.5, and observing whether or not a color change occurs when magnesium ions are added to the solution. If a color change occurs, complexation has taken place.

Hammett-sigma values ($\sigma$) are standard values used to predict the electron-withdrawing or electron-donating effect of substituents on phenyl rings. Such values can be calculated according to standard procedures described, e.g. in *Steric Effects in Organic Chemistry*, John Wiley & sons, Inc., pp. 570–574 (1956) and *Progress in Physical Organic Chemistry*, Vol. 2, Interscience Publishers, pp. 333–339 (1964). Hammett-sigma values for some representative substituents are listed in the text by March, *Advanced Organic Chemistry: Reactions, Mechanisms, and Structure*, McGraw-Hill Book Company, New York, pp. 238–241 (1968). The cumulative Hammett-sigma values shown herein are for substituents on the 3-, 4- and 5-positions only.

Any substituent, or combination thereof, can be used on the phenyl rings which will give the desired electronegative effect. Generally, the useful substituents are considered more electron-withdrawing than a single chloro group. However, substituents which are less electron-withdrawing than chloro can be used in the appropriate positions as long as they are used with other substituents more electron-withdrawing than chloro which provide the desired cumulative effect.

Representative substituents include halo (fluoro, chloro, bromo, etc.), nitro, sulfo, sulfomoyl (i.e. $-SO_2NR_1R_2$ wherein $R_1$ and $R_2$ are independently hydrogen, substituted or unsubstituted alkyl of 1 to 12 carbon atoms, e.g. methyl, ethyl, isopropyl, benzyl, dodecyl, chloromethyl, etc., cycloalkyl of 4 to 6 carbon atoms, e.g. cyclobutyl, cyclohexyl, etc. as well as a chain of alkylene or cycloalkylene groups separated by oxy or thio linkages), cyano, carboxy, substituted or unsubstituted haloalkyl (e.g. mono-, di- or trihaloalkyl wherein the alkyl has from 1 to 12 carbon atoms, e.g. chloromethyl, dibromomethyl, 1,2-dichloroethyl, etc.), carboxamide, substituted or unsubstituted carboxyalkyl (wherein the alkyl has from 1 to 12 carbon atoms as defined above for $R_1$) and substituted or unsubstituted sulfoalkyl (wherein the alkyl has from 1 to 12 carbon atoms as defined above for $R_1$), and others known to one of ordinary skill in organic chemistry.

Particularly useful substitutents include chloro, sulfonamido and substituted or unsubstituted sulfoalkyl as defined above. It is also preferred that the compounds of this invention have the same substituents in the 3-, 4- or 5-position of both phenyl rings of the compound. Most preferably, the substituents are in both of either the 3- or 5-position.

Representative novel cyanoformazan derivatives of this invention include the following compounds, along with the cumulative Hammett-sigma ($\sigma$) values of the phenyl ring substituents other than the 2-hydroxy:

1,5-bis(2-hydroxy-3,5-dichlorophenyl)-3-cyanoformazan, $\sigma$ of about +0.46, 1,5-bis(2-hydroxy-5-sulfamoylphenyl)-3-cyanoformazan, $\sigma$ of about +0.57, 1,5-bis[2-hydroxy-5-(N-butylsulfamoyl)phenyl]-3-cyanoformazan, $\sigma$ of about +0.42, 1,5-bis[2-hydroxy-5-(N-hexylsulfamoyl)phenyl]-3-cyanoformazan, $\sigma$ of about +0.42, 1,5-bis[2-hydroxy-5-(N-octylsulfamoyl)phenyl]-3-cyanoformazan, $\sigma$ of about +0.40, 1,5-bis[2-hydroxy-5-(N-dodecylsulfamoyl)phenyl]-3-cyanoformazan, $\sigma$ of about +0.40, 1,5-bis[2-hydroxy-5-(N,N-diethylsulfamoyl)phenyl]-3-cyanoformazan, $\sigma$ of about +0.40, 1,5-bis(2-hydroxy-5-cyanophenyl)-3-cyanoformazan, $\sigma$ of about +0.66, 1,5-bis[2-hydroxy-3-chloro-5-(N-butylsulfamoyl)phenyl]-3-cyanoformazan, $\sigma$ of about +0.65, and 1,5-bis(2-hydroxy-3-methylsulfonylphenyl)-3-cyanoformazan, $\sigma$ of about +0.72.

The first compound in the above list is preferred in the practice of the assay of this invention.

Other cyanoformazans useful in the practice of this invention include the following compounds (and $\sigma$ values):

1,5-bis(2-hydroxy-5-carboxyphenyl)-3-cyanoformazan, $\sigma$ of about +0.41, 1,5-bis(2-hydroxy-4-carboxyphenyl)-3-cyanoformazan, $\sigma$ of about +0.35, 1,5-bis(2-hydroxy-3-chloro-5-carboxyphenyl)-3-cyanoformazan, $\sigma$ of about +0.64, 1,5-bis(2-hydroxy-4-nitrophenyl)-3-cyanoformazan, $\sigma$ of about +0.71, 1,5-bis(2-hydroxy-5-nitrophenyl)-3-cyanoformazan, $\sigma$ of about +0.78, and 1,5-bis(2-hydroxy-3-sulfo-5-chlorophenyl)-3-cyanoformazan, $\sigma$ of about +0.32.

The novel compounds of this invention can be prepared using standard starting materials and the following general procedure: (1) a 2-hydroxyaniline substituted with the appropriate substituent(s) in the 3-, 4- or 5-position is reacted with sodium nitrite in hydrochloric acid, and (2) the resulting diazooxide is reacted with cyanoacetic acid in an azo coupling reaction to provide the cyanoformazan derivative. Detailed preparations of several compounds are provided in Examples 1–9 below.

The cyanoformazan compounds described herein have varying degrees of solubility in aqueous solution depending upon the phenyl ring substituents they have. If they are water-soluble, they can be dissolved in water or a buffer to form an aqueous composition. Since many of the compounds have limited water solubility, a suitable anionic or nonionic surfactant is preferably used with them to promote solubility. Surfactants having a positive charge are not generally useful because they may cause precipitation of the cyanoformazan compound.

Suitable nonionic surfactants are too numerous to mention but examples of such include: alkylarylpolyethoxy alcohols e.g. those marketed under the TRITON trademark from Rohm and Haas (Philadelphia, Pa., U.S.A.), e.g. TRITON X-100 and X-305, p-alkylaryloxypolyglycidols, e.g. SURFACTANT 10G available from Olin Corp. (Stamford, Conn., U.S.A.) and TWEEN 80 available from ICI Americas, Inc. (Wilmington, Del., U.S.A.), and fluorocarbon surfactants, e.g. ZONYL FSN available from DuPont (Wilmington, Del., U.S.A.).

A variety of anionic surfactants can also be used. Representative surfactants include sodium dodecyl sulfate, sodium octyl sulfate, and others known in the art.

Water-miscible organic solvents may also be included in the analytical composition in minor amounts to promote solubility of the cyanoformazan derivative. Such solvents include alcohols, N, N-dimethylformamide, dimethylsulfoxide, acetone, acetonitrile, etc.

The composition of this invention is buffered to a pH of from about 8.5 to about 10.5 with one or more suitable buffers, e.g. 2-(N-cyclohexylamino)ethane sulfonic acid (CHES), bicine, L-arginine, cyclohexylaminopropane sulfonic acid (CAPS) and others reported by Good et al in *Biochem.*, 5, 467 (1966), and *Anal. Biochem.*, 104, 300 (1980). Preferably, the composition is buffered to a pH of from about 9 to about 10.

Where a fluid to be assayed contains calcium ions in addition to magnesium ions, a suitable calcium ion chelating agent can be used to complex the calcium ions thereby preventing them from complexing with the cyanoformazan compound. A suitable chelating agent is 1,2-bis(o-aminophenoxy)ethane-N,N,N',N'-tetraacetic acid (also known as BAPTA), and other compounds described by Tsien in *Biochem.*, 19, pp. 2396-2404 (1980).

Generally, the cyanoformazan compound is present in the composition of the present invention at a concentration of at least about 5, and preferably from about 20 to about 500, $\mu$molar. The concentration of buffer to achieve the desired pH is within the skill of a worker in the art. The surfactant is generally present in an amount of at least about 0.1, and preferably from about 0.2 to about 0.4, g/ml of solution.

The compositions of this invention can be used to advantage to assay a wide variety of aqueous liquids, e.g. industrial, farm and residential wastewater, food and pharmaceutical processing solutions, food stuffs, groundwater, seawater, biological fluids, etc. The invention is particularly useful for determining magnesium ions in various human and animal biological fluids, e.g. whole blood, blood sera and plasma, urine, lymph fluid, spinal fluid, sputum, homogenized tissue, stool secretions, etc. The practice of this invention is particularly important for the clinical assay of serum or urine.

A solution assay is generally carried out by contacting and mixing the composition described herein with a sample of fluid suspected of containing magnesium ions in a suitable container (e.g. test tube, petri dish, beaker, cuvette, etc.). The resulting solution is mixed for a relatively short time at any suitable temperature (generally at least about 25° C.). The solution is then evaluated by measuring the shift in spectral absorption caused by the complexation of the cyanoformazan derivative and magnesium ions at an appropriate wavelength using suitable colorimetric detection equipment. In many instances, the preferred cyanoformazan derivatives listed above form complexes with magnesium ions which can be detected at a wavelength greater than about 600 nm whereas the derivative alone exhibits maximum absorption at a wavelength less than about 600 nm.

The assay can also be carried out by contacting a porous absorbent material, e.g. paper strip, containing the sample of fluid to be tested, with the composition of this invention. The magnesium ions in the fluid can migrate into and throughout the absorbent material and complex with the cyanoformazan to initiate the dye shift needed for magnesium ion determination.

Alternatively, the method of this invention can be practiced in a "dry" assay which is carried out with a dry analytical element. Such an element can be an absorbent carrier material, i.e. a thin sheet or strip of self-supporting absorbent or bibulous material, such as filter paper or strips, which contains the novel compound or a dried residue of the composition of this invention. Such elements are known in the art as test strips, diagnostic elements, dip sticks, diagnostic agents and the like.

When employed in dry analytical elements, the composition of this invention can be incorporated into a suitable absorbent carrier material by imbibition or impregnation, or can be coated on a suitable material. Alternatively, it can be added to the element during an assay. Useful carrier materials are insoluble and maintain their structural integrity when exposed to water or physiological fluids. They can be prepared from paper, porous particulate structures, cellulose, porous polymeric films, glass fiber, woven and nonwoven fabrics (synthetic and nonsynthetic) and the like. Useful materials and procedures for making such elements are well known in the art as exemplified by U.S. Pat. No. 3,092,465 (issued Jun. 4, 1963 to Adams et al), U.S. Pat. No. 3,802,842 (issued Apr. 9, 1974 to Lange et al), U.S. Pat. No. 3,915,647 (issued Oct. 28, 1975 to Wright), U.S. Pat. No. 3,917,453 (issued Nov. 4, 1975 to Milligan et al), U.S. Pat. No. 3,936,357 (issued Feb. 3, 1976 to Milligan et al), U.S. Pat. No. 4,248,829 (issued Feb. 3, 1981 to Kitajima et al), U.S. Pat. No. 4,255,384 (issued Mar. 10, 1981 Kitajima et al), and U.S. Pat. No. 4,270,920 (issued Jun. 2, 1981 to Kondo et al).

A dry assay can be practiced to particular advantage with an analytical element comprising a support having thereon at least one porous spreading zone as the absorbent carrier material. The spreading zone can be prepared from any suitable fibrous or non-fibrous material or mixtures of either or both as described in U.S. Pat. No. 4,292,272 (issued Sep. 29, 1981 to Kitajima et al), U.S. Pat. No. 3,992,158 (issued Nov. 16, 1976 to Przybylowicz et al), U.S. Pat. No. 4,258,001 (issued Mar. 24, 1981 to Pierce et al) and U.S. Pat. No. 4,430,436 (issued Feb. 7, 1984 to Koyama et al) and Japanese Patent Publication 57(1982)-101760 (published Jun. 24, 1982).

In the elements, the cyanoformazan derivative is generally present in a coverage of at least about 0.1, and preferably from about 0.2 to about 1, $g/m^2$. Other reagents and materials (including buffer) are present in coverages within the skill of a worker in the art.

More details of preferred elements which can be used in a dry assay for magnesium ions are provided in copending and commonly assigned U.S. Ser. No. 857,219, filed on even date herewith by Smith-Lewis et al and entitled ANALYTICAL ELEMENT AND METHOD FOR DETERMINATION OF MAGNESIUM IONS, now U.S. Pat. No. 4,753,890.

The assay using an element can be manual or automated. In general, in using the dry elements, magnesium ion determination is made by taking the element from a supply roll, chip packet or other source and physically contacting it with a sample (e.g. 1 to 200 μl) of the liquid to be tested so that the sample is mixed with the cyanoformazan derivative in the element. Such contact can be accomplished in any suitable manner, e.g. dipping or immersing the element into the sample or, preferably, by spotting the element by hand or machine with one or more drops of the sample with a suitable dispensing means so that the liquid sample mixes with the reagents within the element.

After sample application, the element is exposed to any conditioning, such as incubation, heating or the like, that may be desirable to quicken or otherwise facilitate obtaining any test result.

Determination of magnesium ions is achieved by measuring the amount of dye shift resulting from complexation of the cyanoformazan derivative with the magnesium ions in the test sample using suitable equipment and procedures.

It is to be understood that not every cyanoformazan included in the scope of the method of this invention may be useful in both a solution and dry assay. For example, some compounds, namely those having one or more carboxy or nitro substituents may be more useful in solution assays than dry assays. Other compounds may be more useful in dry assays than solution assays. Matching the compounds with a suitable assay is within the skill of a worker in the art.

In the following examples illustrating the practice of this invention, the materials used were obtained from the following sources: TRITON X-100 nonionic surfactant from Rohm and Haas (Philadelphia, Pa., U.S.A.), bovine serum albumin from Miles Laboratories (Elkhart, Ind., U.S.A.), 2,4-dichloro-6-nitrophenol and other reagents from Aldrich Chemical Co. (Milwaukee, Wis., U.S.A.), and the remainder from Eastman Kodak Company (Rochester, N.Y., U.S.A.).

EXAMPLE 1

Synthesis of 1,5-bis(2-hydroxy-3,5-dichlorophenyl)-3-cyanoformazan

The synthesis of 1,5-bis(2-hydroxy-3,5-dichlorophenyl)-3-cyanoformazan was carried out in the following manner.

Synthesis of 2-amino-4,6-dichlorophenol

The starting material, 2,4-dichloro-6-nitrophenol (260 g, 1 mole, 20% in water), was mixed with methanol (2 liters) and platinum oxide catalyst, and the resulting slurry was reacted with hydrogen at 4.2 kg/cm$^2$ (60 psi) and room temperature.

The resulting solution was filtered to remove the catalyst and concentrated hydrochloric acid (150 ml) was added to the filtrate. The methanol was then removed by evaporation and the residual solid was redissolved in hot water (2 liters) with a little concentrated HCl added. The solution was filtered to remove dark, insoluble material and cooled to 30° C. Dilute NaOH solution was added until the pH was about 6, and the mixture was chilled in an ice bath. The resulting white solid was filtered off and dried at room temperature under nitrogen. The compound yield was about 142 g (80% of theoretical) and it had a m.p. of 93°–95° C.

Synthesis of Cyanoformazan Derivative

The product of the previous step (72 g, 0.4 mole) was dissolved in a solution of 50% NaOH (30 g) in water (500 ml). Sodium nitrite (30 g, 0.43 mole) was added to the mixture with stirring until the salt was dissolved. The resulting solution was dripped into a mixture of concentrated HCl (200 ml) and ice. During the addition, the temperature was kept below 5° C. by external cooling and occasional addition of ice. After the addition was complete, the slurry was stirred for 15 minutes further, and the resulting yellow, solid diazo oxide was filtered off and washed with water. Without drying this solid, it was redissolved in N,N-dimethylformamide (1500 ml) with slight warming.

The resulting diazo oxide solution was run into a solution of cyanoacetic acid (40 g, 0.47 mole) in water (500 ml) and 50% NaOH solution (200 ml). The reaction temperature was kept below 0° C. with cooling and addition of ice. The total volume at completion was about 3 liters. The mixture became thick with precipitated dye and required stirring. After addition of the diazo oxide, the slurry was stirred in the ice/methanol bath for an hour, then warmed to 50° C. to dissolve the dye. Glacial acetic acid was added until the mixture was acidic, and filtration was carried out while the mixture was still warm. The resulting solid was washed with water and dried under vacuum at 80° C. under nitrogen.

The resulting dry, crude solid was added to N,N-dimethylformamide (700 ml) with heating, and glacial acetic acid (700 ml) was added to dissolve the dye under boiling conditions. After chilling and filtration, the resulting crystalline dye was washed with methanol and dried under vacuum to yield 65 g (77% theoretical) having a m.p. of 208°–210° C.

The product was evaluated by elemental analysis which confirmed the identity of the cyanoformazan derivative. Theoretical: C=40.1, H=1.7, N=16.7. Found: C=39.9, H=1.8, N=16.5. The derivative exhibited maximum absorption at 536 nm before complexation with magnesium ions and at 648 nm after complexation.

EXAMPLES 2–9

Preparation of other derivatives

A number of other cyanoformazan derivatives useful in the present invention were prepared in the following manner.

The starting materials, 3-amino-4-hydroxybenzene sulfonamides, were prepared using the standard synthetic method (Kermack et al, *J. Chem. Soc.*, 608, 1939):

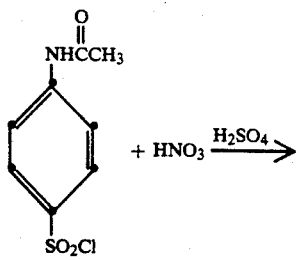

+ HNO₃ $\xrightarrow{H_2SO_4}$

The starting materials described above were used to prepare some of the cyanoformazan derivatives shown in Table I below according to the procedure described in Example 1 above. Other derivatives were similarly prepared using 2-hydroxyaniline as a starting material. Table I below lists the derivatives prepared as well as analytical and absorption data for each.

The dye-Mg$^{++}$ complex absorption in Table I were measured in a buffered composition containing 2-(N-cyclohexylamino)ethane sulfonic acid buffer (0.2 molar, pH 10), sodium chloride (0.15 molar) and TRITON X-100 surfactant (3%).

TABLE I

| Cyanoformazan Derivative | Absorption ($\lambda_{max}$, nm) Derivative | Derivative-Mg$^{++}$ Complex | Elemental Analysis Theoretical | Found |
|---|---|---|---|---|
| Example 2: 1,5-bis(2-hydroxy-5-cyanophenyl)-3-cyanoformazan | 528 | 620 | C = 56.1, H = 3.6 N = 27.0 | C = 56.2, H = 3.9 N = 27.6 |
| Example 3: 1,5-bis[2-hydroxy-5-(N,N'-diethylsulfonamido-phenyl]-3-cyanoformazan | 522 | 620 | C = 47.9, H = 5.3 N = 17.8 | C = 47.1, H = 5.1 N = 17.4 |
| Example 4: 1,5-bis[2-hydroxy-5-(N-hexylsulfamoyl)phenyl]-3-cyanoformazan | 520 | 618 | C = 51.4, H = 6.1 N = 16.1 | C = 50.9, H = 6.1 N = 15.8 |
| Example 5: 1,5-bis-[2-hydroxy-5-(N-dodecylsulfamoyl)phenyl]-3-cyanoformazan | 520 | 618 | C = 58.8, H = 7.9 N = 12.6 | C = 59.1, H = 7.8 N = 12.4 |
| Example 6: 1,5-bis(2-hydroxy-3-chloro-5-carboxyphenyl)-3-cyanoformazan | 550 | 608 | C = 43.9, H = 2.1 N = 16.0 | C = 43.7, H = 3.0 N = 15.8 |
| Example 7: 1,5-bis(2-hydroxy-5-methylsulfophenyl)-3-cyano-formazan | 536 | 614 | C = 43.9, H = 3.5 N = 16.0 | C = 43.3, H = 3.6 N = 15.7 |
| Example 8: 1,5-bis[2-hydroxy-3-chloro-5-(N-butylsulfamoyl)-phenyl]-3-cyanoformazan | 552 | 619 | C = 42.6, H = 4.4 N = 15.8 | C = 41.9, H = 4.3 N = 15.4 |
| Example 9: 1,5-bis[2-hydroxy-5-(N-octylsulfamoyl)phenyl]-3-cyanoformazan | 520 | 618 | C = 54.3, H = 6.8 N = 14.8 | C = 53.9, H = 6.7 N = 14.6 |

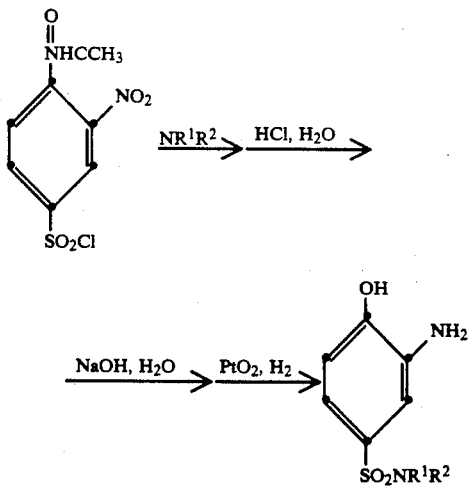

wherein R$^1$ and R$^2$ are defined above.

Other starting materials were prepared as follows:

A 3-amino-5-chloro-4-hydroxybenzene sulfonamide was prepared by direct chlorination of the 3-acetamido-4-hydroxybenzene sulfonamide followed by removal of the acetyl by acid hydrolysis. A cyanoaminophenol was prepared by catalytic reduction of the known nitrocyanophenol (*J. Chem. Soc.*, 643, 1949). A 3-amino-4-hydroxyphenylmethyl sulfone was made by nitration of the known 4-acetamidobenzene sulfinic acid (Smiles et al, *Org. Syn.* coll. v-1,8).

EXAMPLE 10

Dye-Magnesium Ion Complexation

A solution of 1,5-bis(2hydroxy-3,5-dichlorophenyl)-3-cyanoformazan (50 μmolar) was prepared in dimethylsulfoxide (DMSO). A sample of this solution (20 μl) was added to 2 ml of buffer solution (pH 10) containing 0.2 molar 2-(N-cyclohexylamine)ethanesulfonic acid, 0.15 molar NaCl and 3% TRITON X-100 nonionic surfactant.

The absorbance of the resulting solution was measured with a standard spectrophotometer at room temperature. Magnesium ions (400 μmolar) were then added to the buffered solution and the absorbance was measured again. The two absorption scans are shown in the Figure. Complexation of the cyanoformazan derivative with magnesium ions causes a significant absorption shift.

A number of cyanoformazans outside the scope of this invention were prepared according to procedures similar to that in Example 1 above, and tested in an assay for magnesium ions as described above. The compounds tested were:

Control A: 1,5-bis(2-hydroxy-3-chlorophenyl)-3-cyanoformazan,
Control B: 1,5-bis(2-hydroxy-3,5,6-trichlorophenyl)-3-cyanoformazan,
Control C: 1,5-bis(2-hydroxy-3,5-dichloro-6-methylphenyl)-3-cyanoformazan.

None of these compounds were acceptable in an assay for magnesium ions. Control A did not successfully complex with magnesium ions at pH 10. It was determined that this derivative requires a pH higher than 10.5 for acceptable complexing with magnesium ions. Controls B and C, likewise, did not complex with magnesium ions at pH 10, but required a pH greater than 11 for significant complexation.

EXAMPLE 11

Stability of Dye-Mg Ion Complex

The example was carried out to determine the stability of the complex formed between magnesium ions and a cyanoformazan dye of this invention.

Increasing amounts of magnesium ions (up to 700 μmolar) were added to a buffered solution of 1,5-bis(2-hydroxy-3,5-dichlorophenyl)-3-cyanoformazan prepared like that described in Example 10. The absorbance of the solution was measured at the spectra maximum after each increment of ions was added. The fraction of dye complexed was determined by measuring the difference in absorbance with and without ions at the absorbance maximum of the dye-Mg ion complex. This provided the determination of magnesium ions in each test. It was determined that the complex was highly stable as most of the dye remained complexed over the range of magnesium ion concentration.

The invention has been described in detail with particular reference to preferred embodiments thereof, but it will be understood that variations and modifications can be effected within the spirit and scope of the invention.

We claim:

1. A method for the determination of magnesium ions comprising the steps of:

A. at a pH of from about 8.5 to about 10.5 and in the presence of a calcium ion chelating agent, contacting a sample of a human or animal biological fluid suspected of containing magnesium ions with a 1,5-bis(2-hydroxyphenyl)-3-cyanoformazan substituted in at least one of the 3-, 4- and 5-positions of either phenyl moiety with a substituent such that the cumulative Hammett-sigma value of said substituents is greater than about 0.35, said substituents selected from the group consisting of halo, sulfamoyl, N-alkylsulfamoyl wherein said alkyl has 1 to 12 carbon atoms, N,N-dialkylsulfamoyl wherein each of said alkyl groups independently has 1 to 12 carbon atoms, cyano, haloalkyl wherein said alkyl has 1 to 12 carbon atoms, carboxamide, carboxyalkyl wherein said alkyl has 1 to 12 carbon atoms, and sulfoalkyl wherein said alkyl has 1 to 12 carbon atoms, said cyanoformazan being capable of complexing with magnesium ions at a pH of from about 8.5 to about 10.5, and B. detecting the color change resulting from the complexing of magnesium ions with said cyanoformazan.

2. The method of claim 1 carried out at a pH of from about 9 to about 10.

3. The method of claim 1 wherein said biological fluid is serum or urine.

4. The method of claim 1 carried out in the presence of a nonionic or anionic surfactant in step A.

5. The method of claim 1 wherein said cyanoformazan is selected from the group consisting of:

1,5-bis(2-hydroxy-3,5-dichlorophenyl)-3-cyanoformazan, 1,5-bis(2-hydroxy-5-sulfamoylphenyl)-3-cyanoformazan, 1,5-bis[2-hydroxy-5-(N-butylsulfamoyl)phenyl]-3-cyanoformazan, 1,5-bis[2-hydroxy-5-(N-hexylsulfamoyl)phenyl]-3-cyanoformazan, 1,5-bis[2-hydroxy-5-(N-octylsulfamoyl)phenyl]-3-cyanoformazan, 1,5-bis[2-hydroxy-5-(N-dodecylsulfamoyl)phenyl]-3-cyanoformazan, 1,5-bis[2-hydroxy-5-(N,N-diethylsulfamoyl)phenyl]-3-cyanoformazan, 1,5-bis(2-hydroxy-5-cyanophenyl)-3-cyanoformazan, 1,5-bis[2-hydroxy-3-chloro-5-(N-butylsulfamoyl)phenyl]-3-cyanoformazan, and 1,5-bis(2-hydroxy-3-methylsulfonylphenyl)-3-cyanoformazan.

6. The method of claim 5 wherein said cyanoformazan is 1,5-bis(2-hydroxy-3,5-dichlorophenyl)-3-cyanoformazan.

7. The method of claim 1 wherein said cyanoformazan has the same substituents in both or either the 3- or 5-position of said phenyl moieties.

8. The method of claim 1 wherein said color change is detected at a wavelength greater than about 600 nm.

9. The method of claim 1 wherein said cyanoformazan is substituted with one or more substituents selected from the group consisting of chloro, sulfamoyl and sulfoalkyl wherein said alkyl has 1 to 12 carbon atoms.

* * * * *